(12) United States Patent
Grimes et al.

(10) Patent No.: US 7,235,376 B2
(45) Date of Patent: Jun. 26, 2007

(54) GASTRIN HORMONE IMMUNOASSAYS

(75) Inventors: Stephen Grimes, Davis, CA (US); John Little, Cambridgeshire (GB); Lorraine McLoughlin, Cambridgeshire (GB)

(73) Assignee: Receptor Biologix, Inc., South San Francisco, CA (US)

( * ) Notice: Subject to any disclaimer, the term of this patent is extended or adjusted under 35 U.S.C. 154(b) by 0 days.

(21) Appl. No.: 10/813,336

(22) Filed: Mar. 29, 2004

(65) Prior Publication Data

US 2005/0069966 A1    Mar. 31, 2005

Related U.S. Application Data

(60) Provisional application No. 60/458,244, filed on Mar. 28, 2003.

(51) Int. Cl.
- G01N 33/53 (2006.01)
- G01N 33/537 (2006.01)
- G01N 33/543 (2006.01)
- C07K 16/00 (2006.01)

(52) U.S. Cl. .................. 435/7.94; 436/540; 530/391.1

(58) Field of Classification Search ................ 435/7.1, 435/7.92–7.95; 436/518, 540; 530/388.2, 530/388.24, 391.1
See application file for complete search history.

(56) References Cited

U.S. PATENT DOCUMENTS

| | | | |
|---|---|---|---|
| 4,196,265 A | 4/1980 | Koprowski et al. ............. 435/2 |
| 4,997,950 A | 3/1991 | Murphy et al. .......... 548/304.1 |
| 5,023,077 A | 6/1991 | Gevas et al. .................. 424/88 |
| 5,110,911 A | 5/1992 | Samuel et al. |
| 5,468,494 A | 11/1995 | Gevas et al. ............. 424/195.1 |
| 5,580,563 A | 12/1996 | Tam et al. |
| 5,607,676 A | 3/1997 | Gevas et al. |
| 5,609,870 A | 3/1997 | Gevas et al. ............. 424/184.1 |
| 5,622,702 A | 4/1997 | Gevas et al. ............. 424/184.1 |
| 5,643,735 A * | 7/1997 | Yokoi et al. .................. 435/7.9 |
| 5,688,506 A | 11/1997 | Grimes et al. ........... 424/184.1 |
| 5,731,159 A | 3/1998 | Waldman |
| 5,767,242 A | 6/1998 | Zimmermann et al. |
| 5,785,970 A | 7/1998 | Gevas et al. ............. 424/184.1 |
| 5,843,446 A | 12/1998 | Ladd et al. ............. 424/184.1 |
| 5,866,128 A | 2/1999 | Gevas et al. ............. 424/184.1 |
| 5,869,045 A | 2/1999 | Hellstrom et al. |
| 5,932,412 A | 8/1999 | Dillner et al. .................. 435/5 |
| 5,981,167 A | 11/1999 | Taremi et al. .................. 435/4 |
| 6,169,173 B1 | 1/2001 | Wank ........................ 536/23.5 |
| 6,187,536 B1 | 2/2001 | Weinberg et al. |
| 6,251,581 B1 | 6/2001 | Ullman et al. |
| 6,303,123 B1 | 10/2001 | Grimes et al. ............. 424/184.1 |
| 6,320,022 B1 | 11/2001 | Cutitta et al. |
| 6,359,114 B1 | 3/2002 | Grimes et al. ............. 530/344 |
| 6,548,066 B1 | 4/2003 | Michaeli et al. ......... 424/185.1 |
| 6,565,813 B1 | 5/2003 | Garyantes ................... 422/102 |
| 6,696,262 B2 | 2/2004 | Härkönen |
| 6,861,510 B1 | 3/2005 | Gevas et al. ............. 530/388.1 |
| 2002/0058040 A1* | 5/2002 | Grimes et al. ........... 424/185.1 |
| 2002/0095028 A1 | 7/2002 | Grimes et al. ............. 530/412 |
| 2003/0021786 A1 | 1/2003 | Gevas et al. ............. 424/185.1 |
| 2003/0049698 A1 | 3/2003 | Wang |
| 2003/0068326 A1 | 4/2003 | Gevas et al. ............. 424/185.1 |
| 2003/0082643 A1 | 5/2003 | Hudson et al. |
| 2003/0086941 A1 | 5/2003 | Michaeli et al. ......... 424/185.1 |
| 2003/0091574 A1 | 5/2003 | Gevas et al. ............. 424/155.1 |
| 2003/0232399 A1 | 12/2003 | Robertson et al. |
| 2004/0001842 A1 | 1/2004 | Michaeli et al. ......... 424/185.1 |
| 2005/0025770 A1 | 2/2005 | Gevas et al. ............. 424/155.1 |
| 2005/0169979 A1 | 8/2005 | Michaeli et al. ......... 424/184.1 |
| 2005/0187152 A1 | 8/2005 | Gevas et al. .................. 514/12 |
| 2006/0020119 A1 | 1/2006 | Grimes et al. ........... 530/388.1 |
| 2006/0039911 A1 | 2/2006 | Gevas et al. ............. 424/145.1 |
| 2006/0140962 A1 | 6/2006 | Gevas et al. ............. 424/155.1 |

FOREIGN PATENT DOCUMENTS

| | | |
|---|---|---|
| EP | 0380230 | 8/1990 |
| EP | 0818680 | 1/1998 |
| EP | 1579863 | 9/2005 |
| WO | WO 90/08774 | 8/1990 |
| WO | WO 95/13297 | 5/1995 |
| WO | WO 98/51337 | 11/1998 |
| WO | WO 99/59612 | 11/1999 |
| WO | WO 99/59628 | 11/1999 |
| WO | WO 99/59631 | 11/1999 |
| WO | WO 01/77685 A2 | 10/2001 |
| WO | WO 02/076499 | 10/2002 |
| WO | WO 2004/023148 | 3/2004 |
| WO | WO 04/088326 | 10/2004 |

(Continued)

OTHER PUBLICATIONS

Rehfeld et al., "Residue-specific immunochemical sequence prediction" (1994) Journal of Immunological Methods 171:139-142.*

(Continued)

Primary Examiner—Long V. Le
Assistant Examiner—Christine Foster
(74) Attorney, Agent, or Firm—Fish & Richardson P.C.; Stephanie Seidman; Paula K. Schoeneck (57) ABSTRACT

The invention provides assay methods for the detection and quantitation of gastrin hormones, including total and free gastrin hormone in a sample. ELISA-type heterogeneous phase assays suitable for use with biological fluid samples such as blood, plasma or other bodily fluids of a mammal, particularly a human subject are provided. The method provides a precise assay for the amounts of free and total G17 and G34 in biological fluid samples, as well as the amounts of free and total Gly-extended G17, and Gly-extended G34. Also provided are methods of determining suitable treatment for patient suffering from a gastrin hormone-mediated disease or condition employing gastrin hormone immunoassays.

18 Claims, 2 Drawing Sheets

FOREIGN PATENT DOCUMENTS

| WO | WO 05/095459 | 10/2005 |
| WO | WO 06/008649 | 1/2006 |
| WO | WO 06/016275 | 2/2006 |
| WO | WO 06/032980 | 3/2006 |

OTHER PUBLICATIONS

Goetze et al. "Impact of Assay Epitope Specificity in Gastrinoma Diagnosis" (Feb. 2003) Clinical Chemistry 49: 333-334.*
Biochemistry. Berg, Jeremy M.; Tymoczko, John L.; and Stryer, Lubert. New York: W. H. Freeman and Co.; 2002, Sections 4.3.1-4.3.3 and Figure 4.35.*
Azuma et al. "Immunocytochemical evidence for differential distribution of gastrin forms using region-specific monoclonal antibodies" (1986) Gastroenterol Jpn 21:319-324.*
Watson, S. Exp. Opin. Invest. Drugs, 1995, 1253-1266, vol. 4.
Watson, et al., Gastrin Receptors in Gastrointestinal Tumors, 1993, 1-91, CRC press, Boca Raton, FL.
Caplin, et al., Journal of Hepatology, 1999, 519-526, vol. 30.
Henwood, et al., British Journal of Surgery, 2001, 564-568, vol. 88.
Watson et al., Int. J. Cancer, 1998, 873-877, vol. 75.
Watson et al., Int. Cancer, 1999, 248-254, vol. 81.
Watson, et al., Cancer Research, 1996, 880-885, vol. 56.
Watson, et al., Cancer Research, 2001, 625-631, vol. 61.
Watson, et al., Reports, 1991, 866-871, vol. 83, J. Natl Cancer Inst.
Watson, et al., Growth Enhancing effects of Gastrin, 1998, 554-558, Br. J. Cancer vol. 59.
Watson, et al., Exp. Opin. Invest. Drugs, 1995, 1253-1266, vol. 4.
Kovacs, et al, Gastroenterology, 1989, 1406-1413, vol. 97.
Kovacs et al., American Journal Physiology, 1997, G399-403, vol. 273 (2 Pt 1).
Vaananen et al., European J. Gastrolenterology, 2003, 885-891, vol. 15 (Pt 8).
Du et al., J Biotechnology, 2003, 87-100, vol. 106 (1).
Tetin et al., Current Pharm. BioTechnol. 2004, 9-16, vol. 5 (Pt 1).
Onorato et al., NY Acad. Sci. 1998, 277-290, vol. 1998.
Plested et al., Methods Mol. Med. 2003, 243-261, vol. 71.
Rondeel, et al., Expert Rev. Mol. Diagnos. 2002, 226-232, vol. 2 (Pt 3).
Bailey et al., Methods Mol. Biol. 1994, 449-459, vol. 32.
Sugano et al., The Journal of Biological Chemistry, 1986, 11724-11729, vol. 380.
Varro et al., Ann Clin Biochem, 2003, 472-480, vol. 40.
Rahier et al., Biosynthesis of Gastrin, Gastronenterology, 1987, 1146-1152, vol. 92.
Kokthary et al., Regulatory Peptides, 1987, 71-84, vol. 17.
Ardill et al., QJ Med, 1998; 739-742, vol. 91.
Seva, et al., Science, 1994, 410-412, vol. 265.
Smith et al., The British Journal of Surgery, 1998, 1285-1289, vol. 85.
Todisco et al., The Journal of Biological Chemistry, 1995, 28337-28341, vol. 270.
Varro et al., The Journal of Biological Chemistry, 1994, 20764-20770, vol. 269.
Dickinson et al., The Journal of Biological Chemistry, 1991, 334-338, vol. 266.
Kelly et al., Journal of Gastroenterology and Hepatology, 1998, 208-214, vol. 13.
Rehfeld et al., Cancer Research, 1989, 2840-2843, vol. 49.
Smith et al., Gut, 2000, 820-824, vol. 47.
Hughes et al., Digestive Diseases, 1976, 201-204, vol. 21.
Jaffe et al., Surgery, 1969, 633-639, vol. 65.
Dockray et al., The Gastrins: Their Production and Biological Activities, 119-139.
Smith et al., Alimentary Pharmacology & Therapeutics, 1231-1247, vol. 14.
Dickinson et al., Gastroenterology, 1995, 1384-1388, vol. 109.
Rehfeld et al., Biochimica et Biophysic Acta, 1972, 364-372, vol. 285.
Nemeth et al., Gut, 1993, 90-95, vol. 34.
Varndell, et al., Experienta, 1983, 713-717, vol. 39.
Wang, et al., Human Progastrin, J. Clin Invest. 1996, 1918-1929, vol. 98.
Watson, et al., Exp. Opin. Ther., 2001, 309-317, vol. 1.
Hoff, et al., Current Opinion in Oncology, 2002-621-627, vol. 14.
Gilliam et al., EJSO, 2004, 536-543, vol. 30.
Makishima, et al., Faseb Journal, 1994, A92, vol. 8 Abs 535.
Smith, et al., Clinical Cancer Research, 2000, 4719-4724, vol. 6.
HSI, MD, Arch Pathol Lab Med, 2001, 289-294, vol. 125.
Cole, Clinical Chemistry, 1997, 2233-2243, vol. 43.
Feurle et al., Pancreas, 1995, 281-286, vol. 10.
Ohning et al., Peptides, 1994, 417-423, vol. 15.
Kovacs et al., Peptides, 1996, 583-587, vol. 17.
Ohning, et al., The American Journal Physiological Society, 1996, G470-476.
Sipponen, et al., Scand J Gastroenterol, 2002, 785-791, vol. 7.
Dockray, et al., Gastroenterology, 1975, 222-230, vol. 68.
Smith, et al., American Journal Physiology, 1996, R1078-R1084, vol. 270.
Smith, et al., American Journal Physiology, 1995, R135-R141, vol. 286.
Smith, et al., American Journal Physiology, 1994, R277-283, vol. 266.
Yanaihara, et al., Gut Peptides, 1979, 26-33.
Abrahm et al., "Development and evaluation of a high affinity species and region specific monoclonal antibody to human gastrin," Gastroenterology, 86(5(2)):1012, (1984).
Aphton Biopharma BIO2005 Presentation, Jun. 19-22, Philadelphia, PA (2005), 26 pages.
Ausubel, ed., "Current Protocols in Molecular Biology," John Wiley & Sons, New York, pp. 11.15.1-11.15.4. (1990).
Blackmore et al. "Autocrine growth stimulation of human renal Wilms' tumour G401 cells by a gastrin-like peptide," International Journal of Cancer, 57:385-391, (1994).
Caplin et al., "Serum gastrin levels and identification of CCK-B-gastrin receptor following partial hepatectomy for liver tumours in man," Gastroenterology, 110(4 suppl.) A1162, (1996).
Caplin et al., "Demonstration of new sites of expression of the CCK-B/gastrin receptor in pancreatic acinar AR42J cells using immunoelectron microscopy," Regulatory Peptides, 84(1-3):81-89, (1999).
Caplin et al., "Effect of gastrin and anti-gastrin antibodies on proliferation of hepatocyte cell lines," Digestive Diseases and Sciences, 46(7):1356-1366, (2001).
Ciccotosto et al., "Expressions, processing, and secretion of gastrin in patients with colorectal carcinoma," Gastroenterology, 109(4):1142-1153, (1995).
"Gastrin 17 vaccine—Aphton: Anti-gastrin 17 immunogen, G17DT," Biodrugs 17(3):223-225 (2003).
Gocyk et al., "Helicobacter pylori, gastrin and cyclooxygenase-2 in lung cancer," Med. Sci. Monit. 6(6):1085-1092 (2000).
Halter et al., "Evaluation of a monoclonal anti-gastrin antibody as a tool for immunoneutralization of gastrin during omeprazole treatment in the rat", *Gastroenterology* 96(5) part 2:A194 (1989).
Harris et al., "An antiapoptotic role for gastrin and the gastrin/CCK-2 receptor in Barrett's esophagus," Cancer Res. 64(6):1915-1919 (2004).
Helander et al., "Immunohistochemical localization of gastrin/CCK-B receptors in the dog and guinea-pig stomach," Acta Physiologica Scandinavica, 159:(4)313-320, (1997).
Herget et al., "Cholecystokinin stimulates Ca2+mobilization and clonal growth in small call lung cancer through CCKA and CCKB/gastrin receptors," Annals of the New York Academy of Sciences, 713:283-297, (1994).
Janeway et al., "Immunobiology: the immune system in health and disease", Fourth Edition, 1999, Elsevier Science Ltd, garland Publishing, p. 544.
Joshi et al., "Gastrin and Colon Cancer: a unifying hypothesis"*Digestive Diseases* 14:334-344 (1996).
Kohler et al., "Continuous cultures of fused cells secreting antibody of predefined specificity", Nature 256:495-497 (1975).
McWilliams et al., "Antibodies raised against the extracellular tail of the CCKB/gastrin receptor inhibit gastrin-stimulated signaling," Regulatory Peptides, 99(2-3):157-161, (2001).

Mishell et al., "Selected Methods in Cellular Immunology" (Chapter 17: Immunoglobulin Producing Hybrid Cell Lines), Freeman and Co., San Francisco, 1980).

Mulholland et al., "Elevated Gastric Acid Secretion in Patients with Barrett's Metaplastic Epithelium" Digestive Diseases and Sciences, 34(9):1329-1334, (1989).

Smith et al., "Characterization of the CCK-C (cancer) receptor in human pancreatic cancer" Int. J. Mol. Medicine 10(6):689-694 (2002).

Smith et al., "Gastrin may have an autocrine/paracrine role in Barrett's oesophagus and oesophageal adenocarcinoma," British Journal of Surgery, 84:706-707, (1997).

Tarasova et al., "Anti-peptide antibodies specific for the gastrin-cholecystokinin-B receptor," Letters in Peptide Science, 1:221-228, (1995).

Tarasova et al., "Endocytosis of gastrin in cancer cells expressing gastrin/CCK-B receptor" Cell and Tissue Research, 287:325-333 (1997).

Thorndyke, "Identification and localization of material with gastrin-like immunoreactivity in the neutral ganglion of a photochordate, Ciona intestinalis." Regulatory Peptides 16:269-279 (1986).

Watson et al., "Antibodies targeting the amino terminal portion of the human CCKB/gastrin receptor inhibit the liver invasion of a human colonic tumor," Gastroenterology 114(4 Part 2): A701 (Abstract # G2899) (Apr. 15, 1998).

Watson et al., "Effect of gastrin neutralization on the progression of the adenoma:carcinoma sequence in the Min mouse model of familial adenomatous polyposis,"Gastroenterology 114(Supplement 1): A701 (Abstract #G2900) (Apr. 15, 1998).

Watson et al., "Growth-promoting action of gastrin on human colonic and gastric tumour cells cultured in vitro" Br. J. Surg. 75(4):342-345 (1988).

Watson et al., "Inhibitory effects of the gastrin receptor antagonist (L-365,260) on gastrointestinal tumor cells," Cancer, 68:1255-1260, (1991).

Watson et al., "Anti-gastrin antibodies raised by gastrimmune inhibit growth of colorectaltumor AP5" Int. J. Cancer, 61(2):233-240 (1995).

Watson et al., "Expression of gastric-CCKB receptor isoforms in gastrointestinal tumor cells: Relationship to gastrin secretion," Proceedings of the American Association for Cancer Research Annual Meeting, 38(0):116 (Abstract 773), (1997).

Watson et al., "Antiserum raised against an epitope of the cholecystokinin B/gastrin receptor inhibits hepatic invasion of a human colon tumor," Cancer research, 60(20):5902-5907, (2000).

Watson et al., "Antibodies raised by gastrimmune inhibit the spontaneous metastasis of a human colorectal tumour AP5LV," European Journal of Cancer, 35(8):1286-1291, (1999).

Watson et al., "Antibodies targeting the Amino Terminal portion of the Human CCKB/gastrin receptor inhibit the liver invasion of a human colonic tumour," Research Presentation, Digestive Disease Week, American Gastroenterological Association (1998), 17 slides.

Watson et al., "Inhibition of gastrin-stimulated growth of gastrointestinal tumour cells by octreatide and the gastrin/cholecystokinin receptor antagonists, proglumide and lorglumide," European Journal of Cancer, 28A(8-9):1462-1467, (1992).

Watson et al., "The in vitro growth response of primary human colorectal and gastric cancer cells to gastrin," International Journal of Cancer, 43:692-696, (1989).

Watson et al., "Therapeutic effect of the gastrin receptor antagonist, CR2093 on gastrointestinal tumour cell growth," British Journal of Cancer, 65(6):879-883, (1992).

* cited by examiner

FIG. 1

Representative Total Gastrin 17 calibration curve

FIG. 2

Representative free gastrin 17 calibration curve

GASTRIN HORMONE IMMUNOASSAYS

RELATED APPLICATIONS

This application claims the benefit of U.S. provisional application 60/458,244 entitled "Gastrin Hormone Assay" filed Mar. 28, 2003 the specification of which is hereby incorporated by reference in its entirety. This application is co-filed on Mar. 29, 2004 with U.S. provisional application 60/577,759 entitled "Monoclonal Antibodies to Gastrin Hormone" the specification of which is hereby incorporated by reference in its entirety.

FIELD OF THE INVENTION

The invention relates to ELISA methods for detecting and/or quantifying a biological peptide, particularly gastrin hormone peptides, in a biological fluid. In particular, the invention relates to methods for detecting and/or quantifying free peptide, and total peptide including antibody-bound peptide in a biological fluid.

BACKGROUND OF THE INVENTION

Although gastrin hormone was first identified one hundred years ago, and was purified in the 1960's, its effects on different tissues in normal and disease tissues is still incompletely understood. One major reason for this gap in knowledge of the gastrin system has been the difficulty in separately detecting and quantifying each of the several forms of gastrin hormone.

In mammals the peptide hormone, gastrin exists in several forms, grouped into two major size classes, "little" gastrin and "big" gastrin, on the basis of the number of amino acid residues in the peptide chain. The "little" gastrin form includes mature gastrin-17 (G17) and glycine-extended G17 (G17-Gly); and "big" gastrin includes gastrin-34 (G34) and glycine-extended G34 (G34-Gly). The mature form of G17 is a major effector of stomach acid secretion and is estimated to be about six times more effective in this role than is G34. The various forms of gastrin are produced in vivo from a precursor peptide, progastrin, by cleavage and in some cases, modification of the cleaved form. Human G34 has the entire seventeen amino acid sequence of G17 at its C-terminal, and, predictably, cross-reacts immunologically with G17.

Mature G17 is modified at both amino- and carboxy-terminal residues: the N-terminal glutamic acid is cyclized to form pyroglutamic acid (pGlu) and the free carboxyl group of the C-terminal phenylalanine residue is amidated by the enzyme, peptidyl α-amidating mono-oxygenase (PAM) to form a C-terminal Phe-$NH_2$. (See Dockray et al., Ann. Rev. Physiol. (2001)63: 119–139).

Mature G17, the predominant form of "little" gastrin in humans, has the amino acid sequence: pEGPWLEEEEE-AYGWMDF-$NH_2$ (SEQ ID NO: 1). G17-Gly is an incompletely processed form of gastrin found as a minor component of "little" gastrin in healthy human subjects and has the amino acid sequence: pEGPWLEEEEEAYGWMDFG (SEQ ID NO: 2).

Gastrin-34, the predominant form of "big" gastrin in humans, has the amino acid sequence: pELGPQGPPHL-VADPSKKEGPWLEEEEEAYGWMDF-$NH_2$ (SEQ ID NO: 3), and glycine-extended gastrin 34 (G34-Gly), has an extra C-terminal glycine residue, having the amino acid sequence: pELGPQGPPHLVADPSKKEGPWLEEEEEAYGWMDFG (SEQ ID NO: 4).

Gastrin is secreted by the pyloric antral-G cells of the stomach in response to gastrin-releasing peptide (GRP). Gastrin secretion is suppressed by gastric acid and the paracrine action of several peptide hormones, most notably, somatostatin. It has long been recognized that gastrin peptides function to stimulate acid secretion in the stomach of healthy individuals, however, it has only recently been shown that these peptides also control proliferation, differentiation and maturation of different cell types in the gastrointestinal (GI) system.

In addition to their local activity in the GI system, G17 and, to a lesser extent, G17-Gly are released into the bloodstream and have been found to increase in the serum of patients afflicted with gastrointestinal disorders and diseases, such as gastric cancer, colorectal cancer, and pancreatic cancer. These gastrin species have more recently also been found to be associated with other diseases not associated with the gastrointestinal tract, including small cell lung cancer (SCLC) and liver metastasized tumors. See for example "*Gastrin and Colon Cancer: a unifying hypothesis*" S. N. Joshi et al., Digestive Diseases (1996) 14: 334–344; and "*Gastrin and colorectal cancer*" Smith, A. M. and Watson, S. A. Alimentary Pharmacology and Therapeutics (2000) 14(10): 1231–1247.

Antibodies are key reagents in numerous assay techniques used in medical, veterinary and other fields. Such tests include many routinely used immunoassay techniques, such as for example, enzyme-linked immunosorbant assays (ELISA), radioimmunoassays (RIA), immunohistochemistry (IHC), and immunofluorescence (IF) assays.

Monoclonal antibodies (MAbs) have unique characteristics that render them superior in many respects to polyclonal antisera and to antibodies purified from polyclonal antisera when used in many of these assays. These attributes include monodeterminant specificity for the target antigen (i.e. specificity for a single epitope), unchanging specificity among different antibody preparations, as well as unchanging affinity and chemical composition over time. Furthermore, MAbs can be produced indefinitely and in unlimited amounts by in vitro methods. These properties are in sharp contrast to those of polyclonal antibodies, which require in vivo immunization methods with the unavoidable associated biological variability and limited antibody production capacity over the lifespan of the immunized animal.

Despite these advantages, differences exist between individual MAbs even though they may be specific for the same epitope. For example, differences between MAbs induced by immunization with a single antigenic epitope region can arise with respect to any or all of the following characteristics: 1) the fine specificity for the molecular composition and tertiary structure of the epitope; 2) the antibody idiotype; 3) the antibody affinity; 4) the antibody allotype; and 5) the antibody isotype. These characteristic differences can affect the behavior of MAbs in a particular immunoassay, such that different MAb isolates raised against the same antigenic region can behave differently in a given assay. Consequently, some MAbs will be superior to others that bind the same epitope when used as reagents in a particular immunoassay.

The immunoassay may be an enzyme-linked immunosorbent assay (ELISA) or a radioimmunoassay (RIA), an immuno-detection assay, such as an ELISPOT, slot-blot, and western blot. As a general guide to such techniques, see for instance, Ausubel et al. (eds) (1987) in "*Current Protocols in Molecular Biology*" John Wiley and Sons, New York, N.Y. Alternatively, the immunoassay may be an immunohistochemical (IHC) staining or immunofluorescence (IF)

procedure for visualization of a gastrin hormone in a tissue sample. See for example "*Principles and Practice of Immunoassay*" (1991) Christopher P. Price and David J. Neoman (eds), Stockton Press, New York, N.Y.

Monoclonal antibodies specific for the N-terminal region and the C-terminal region of G17 have been described. See for example, Azuma et al., *Gastroenterologica Japonica* (1986) 21(4): 319–324; Ohning et al., *Peptides* (1994) 15(3):417–423; Fuerle et al., *Pancreas* (1995) 10(3):281–286; Kovacs et al., *Peptides* (1996) 17 (4): 583–587; Ohning et al., *Am. J. Physiol.* (1996) 271(3 Pt 1):G470–476; Sipponen et al., (2002) Scand. J. Gastroenterol. 37(7): 785–791. However, none of these antibodies were shown, either alone or in combination, to be capable of distinguishing and quantifying each of the forms of gastrin hormone found in biological fluids in normal and disease states.

Anti-gastrin polyclonal antibodies have been shown to be effective in inhibiting gastrin activity ("Inhibition of gastrin activity by incubation with antibodies to the C-terminal tetrapeptide of gastrin" Jaffe et al., *Surgery* (1969) 65(4): 633–639); and non-human anti-gastrin polyclonal antibodies have been applied to therapy in a patient suffering from Zollinger-Ellison syndrome, a pathological condition in which excessive gastrin is produced without stimulation by feeding. See Hughes et al., "*Therapy with Gastrin Antibody in the Zollinger-Ellison Syndrome*" Hughes et al., *Digestive Diseases* (1976) 21(3):201–204. However, these rabbit anti-gastrin antibodies had "at best a short term effect in this patient." (Hughes at p. 204).

Recently, the ratio of amidated to non-amidated gastrin hormone in serum has been suggested as providing an indication of an individual's risk profile for developing duodenal ulcer disease or gastric atrophy. See published U.S. patent application 2003/0049689 entitled "Diagnosis and Treatment of Gastrointestinal Disease" of T. C. Wang.

Until now, MAbs capable of sensitively detecting, and accurately distinguishing each of the G17, G17-Gly, G34, and G34-Gly forms of gastrin hormone have not been available. Furthermore, until the present invention, it was not possible to accurately measure the amounts of each of these forms of gastrin hormone in a sample of biological fluid. Use of the Mabs of the invention in assays for clinical testing more precisely defines the biology of gastrin hormone in normal and disease states and to provides MAb compositions for pharmaceutical use and methods for the prevention and treatment of gastrin-associated diseases and conditions.

SUMMARY OF THE INVENTION

The present invention provides a method for determining the total amount of gastrin hormone including the antibody-bound and free in a biological fluid sample. The method includes the steps of: (a) obtaining a biological fluid sample comprising a gastrin hormone from a patient; (b) providing an immobilized antibody that selectively binds a C-terminal epitope of the gastrin hormone; (c) incubating the sample in the presence of an N-terminal sequence gastrin peptide under suitable conditions for binding of the gastrin hormone in the sample to said antibody to produce an immobilized complex of said antibody bound to the gastrin hormone; (d) washing the immobilized complex to remove N-terminal sequence gastrin peptide, and incubating the complex with a suitable detectable marker-conjugated antibody that selectively binds an N-terminal epitope of gastrin hormone to form an immobilized detectable marker-conjugated antibody complex; (e) washing the immobilized detectable marker-conjugated antibody complex, and incubating with a development reagent; and (f) measuring the developed reagent to determine the total amount of the gastrin hormone in the biological fluid sample.

The invention also provides a method for determining the amount of free gastrin hormone in a biological fluid sample. The method includes the steps of: (a) obtaining a biological fluid sample comprising a gastrin hormone from a patient; (b) providing an immobilized antibody that selectively binds a N-terminal epitope of the gastrin hormone; (c) incubating the sample under suitable conditions for binding of the gastrin hormone in the sample to said antibody to produce an immobilized complex of said antibody bound to the gastrin hormone; (d) washing the immobilized complex to remove unbound components, including said antibody, and reacting the complex with a suitable detectable marker-conjugated antibody that selectively binds an C-terminal epitope bound to the gastrin hormone; (e) washing the immobilized detectable marker-conjugated antibody complex, and incubating with a development reagent; and (f) measuring the developed reagent to determine the amount of free gastrin hormone in the biological fluid sample.

The invention further provides a method for determining the total amount of bound plus free peptide in a biological fluid sample, wherein at least a portion of the peptide is reversibly bound at a first binding sequence. The method includes the following steps: (a) obtaining a biological fluid sample containing the peptide; (b) providing a solid substrate coated with an antibody that selectively binds a first epitope of the peptide which is not present in the first binding sequence; (c) incubating a portion of the sample in the presence of a fragment of the peptide comprising the first binding sequence, but not the first epitope, under suitable conditions for binding of the peptide to said antibody to produce a complex of said antibody bound to the peptide; (d) washing the wells to remove unbound antibody and the fragment of the peptide, and reacting the complex with a suitable detectable marker-conjugated antibody that selectively binds a second epitope of the peptide; (e) washing the wells, and adding a development reagent to the wells; and (f) measuring the developed reagent to determine the total amount of bound plus free peptide in the biological fluid sample.

The invention also provides a method of evaluating a gastrin hormone blocking treatment of a patient suffering from a gastrin hormone-mediated disease or condition. The method includes the steps of: a) obtaining a first sample of biological fluid from the patient prior to or in the early stages of a treatment; b) determining the level of gastrin hormone in the first sample by an immunoassay method; c) performing a diagnosis on the basis of the disease or condition to be treated and the level of gastrin hormone in the first sample; d) administering a treatment to the patient, comprising: a first agent or a substance that generates a first agent which binds gastrin hormone so as to modulate its binding to its target receptor in vivo; e) obtaining a second sample of biological fluid from the patient after a suitable time within which the treatment would have an effect; f) determining the level of total gastrin hormone including bound and free gastrin hormone in a first aliquot of the second sample by an immunoassay method, wherein the first aliquot of the second sample is incubated with (i) a second agent that displaces any gastrin hormone bound by the first agent, and (ii) an immobilized anti-gastrin hormone antibody, wherein the immobilized antibody does not bind the second agent; washing to remove the second agent and adding a detectable antibody that binds the gastrin hormone and does not compete with the immobilized antibody, forming an immunocomplex comprising the immobilized antibody bound to gastrin hormone, the gastrin hormone in turn being bound by the detectable antibody; g) detecting the amount of the detectable antibody in the immunocomplex and thereby determining the amount of total gastrin hormone in the second sample; h) determining the level of free gastrin hormone by repeating steps f) and g) with a second aliquot of the second sample, wherein the incubation in step f) is performed without the second agent; and j) comparing the determined amounts of free gastrin hormone in the first sample with the amounts of free and total gastrin hormone in the second sample so as to determine the efficacy of the gastrin blocking treatment in the patient.

DETAILED DESCRIPTION OF THE INVENTION

The following provides the definitions of terms and phrases as used in this specification:

A "gastrin hormone" or "gastrin hormone form" as used interchangeably herein means any biologically active and/or immunologically cross-reactive gastrin hormone peptides. The major forms of gastrin hormone include, but are not limited to gastrin-17 (G17), whether amidated at the C-terminus or having a free C-terminus; glycine extended gastrin-17 (G17-Gly); gastrin-34 (G34), including both the C-terminally amidated form and the form having a free C-terminus; and glycine extended gastrin-34 (G34-Gly).

As used herein, the term "selective" for a particular a form of gastrin hormone means that the antibody, while being specific for the particular target epitope of a particular form of gastrin hormone, binds each of the forms of gastrin hormone that contain the target epitope. For instance, the C-terminal of mature (amidated) G17 is common to mature G17 and G34. Thus, a MAb that is specific for the target C-terminal epitope found on mature G17 C-terminus is also selective for G17 (and for G34).

The "total amount" of a gastrin hormone form in a sample as used herein means the sum of the amount of free (unbound) gastrin hormone form plus the amount of complexed (bound) gastrin hormone form. The complexed gastrin may be bound by an antibody or other gastrin-binding moiety in the sample.

A "biological fluid" as used herein means any fluid comprising material of biological origin. Preferred biological fluids for use in the present invention include bodily fluids of an animal, especially a mammal, preferably a human subject. The bodily fluid may be any bodily fluid, including but not limited to blood, plasma, serum, lymph, cerebrospinal fluid (CSF), and the like.

A "preservative agent" as used herein means any agent, supplement or additive that reduces the time dependent degradation of gastrin in a sample of biological fluid, or a liquid sample comprising a biological component. Preservative agents useful in the practice of the present invention include any of the many preservative agents well known in the art, including but not limited to general chemical preservatives, such as for instance, sodium azide, EDTA and protease inhibitors, such as for instance, PMSF (Phenylmethylsulfonylfluoride), and aprotinin (e.g. Trasylol), or a biological preservative, such as for instance, heparin.

A "test plate" as used herein means any solid substrate on which multiple fluid samples may be individually assayed according to the methods of the present invention. A "well" of a test plate as used herein means an area of a test plate used as a sample-receiving location of the plate. Typically, the wells of a test plate are formed from depressions in the surface of the plate sufficient to receive and retain the sample volume plus the volume of any buffer or wash fluid added in any of the steps of the assay procedure.

"Measuring" as applied to a target molecule and as used herein means detecting, quantifying or otherwise determining the amount of an analyte or target molecule.

Specifically, the present invention discloses MAbs that are particularly suitable for use in an immunoenzymometric assay (commonly termed an "ELISA" or enzyme-linked immmunosorbent assay) designed to measure the particular form of gastrin hormone in a biological fluid.

MAbs useful in the practice of the present invention include MAbs that selectively bind the N-terminus of gastrin-17 (G17) at an epitope within the amino acid sequence pEGPWLE (SEQ ID NO: 5).

MAbs useful in the practice of the present invention also include MAbs that selectively bind the C-terminus of gastrin-17 (G17) or gastrin-34 (G34) at an epitope within the amino acid sequence EEAYGWMDF-$NH_2$ (SEQ ID NO: 6).

In another aspect, MAbs useful in the practice of the present invention include MAbs that selectively bind the N-terminus of human gastrin-34 (hG34) at an epitope within the amino acid sequence pELGPQG (SEQ ID NO: 7).

In yet another aspect, MAbs useful in the practice of the present invention include MAbs that selectively bind the C-terminus of glycine-extended gastrin-17 (G17-Gly) and glycine-extended gastrin-34 (G34-Gly) at an epitope within the amino acid sequence YGWMDFG (SEQ ID NO: 8).

MAbs useful in the practice of the present invention preferably bind the gastrin hormone form for which they exhibit selective binding with an association constant ($K_a$) of from about $10^6$ to about $10^7$ $LM^{-1}$, preferably the MAbs bind the gastrin hormone form with a $K_a$ from about $10^7$ to about $10^8$ $LM^{-1}$, yet more preferably from about $10^8$ to about $10^9$ $LM^{-1}$, even more preferably from about $10^9$ to about $10^{10}$ $LM^{-1}$, and still more preferably from about $10^{10}$ to about $10^{11}$ $LM^-$, and most preferably from about $10^{11}$ to about $10^{12}$ $LM^{-1}$ The sample to be analyzed according to the methods of the present invention is preferably a sample of biological fluid from a mammal, the sample containing or being suspected of containing an amount of a peptide to be detected, quantitated or otherwise determined. Preferably, the sample contains gastrin hormone in at least one gastrin hormone form. Most preferably, preservative agent having been added to the sample to form a sample mixture and the sample mixture having been frozen within between about 1-about 15 minutes from sample collection from the mammal.

"Suitable conditions" for binding as used herein means conditions of temperature, pH and ionic strength that permit the binding of antibody to its cognate antigen and the enzyme reaction of the marker enzyme label in a reaction in which an enzyme label is conjugated to an antibody used as a detection agent. Such suitable conditions for antibody-antigen binding and for each type of marker enzyme reaction are well known to those of skill in the art and may be determined specifically for each reaction by routine methods without undue experimentation.

As used herein "detectable marker-conjugated antibody" means any labelled antibody, wherein the label provides a detectable signal, such as for instance an enzyme label, or can be detected with another agent, such as a labelled second antibody that can itself be detected by providing a detectable signal, such as for instance a radioactive label, an enzyme label, a fluorescent or luminescent label or a moiety that can be separately detected such as a biotin label, detectable by an avidin conjugated moiety.

As used herein "detectable marker-conjugated antibody complex" is a complex comprising the antibody to which a detectable marker is conjugated, bound to its cognate antigen, which may be for instance, a gastrin hormone. Such a gastrin hormone-antibody complex provides a detectable signal which can be measured and is directly related to the concentration of detectable antibody. Over the preferred range of concentrations, the signal is directly proportional to the concentration of detectable marker-conjugated antibody complex.

"Development reagent" as used herein means a reagent that is developed by the antibody conjugated enzyme. For instance, the development reagent for alkaline phosphatase can be pNPP.

The invention provides assay methods for measuring total (bound and free) gastrin hormone and methods of evaluating gastrin hormone-blocking treatments. These assay methods are described below. The method of evaluating a gastrin hormone-blocking treatment in a patient is particularly valuable in clinical practice, where timing of decisions to proceed with one therapeutic regimen or another may be critical to the outcome for the patient. The method of the present invention provides information on which to base these critical decisions. The method provides a measure of gastrin hormone prior to or in the early stages of treatment (e.g. shortly after vaccination with a gastrin hormone peptide conjugate vaccine, such as that described in U.S. Pat. No. 5,622,702) and provides one or more measurements of total and/or free gastrin hormone after a period in which the treatment is expected to have begun to be effective.

Analytical Methods

There follows a description of the analytical methods (immunoenzymometric assay) of the invention to determine either total (non-complexed plus antibody-complexed) or free (non-complexed) human gastrin hormone (G17, G17-Gly, G34 or G34-Gly) present in biological fluids such as human plasma, by using monoclonal and/or polyclonal antibodies directed to the C-terminus or the N-terminus of the particular molecular form of gastrin hormone that is being assayed. Alternatively, a combination of a polyclonal antibody directed to the C-terminus or to the N-terminus of the molecule may be used in combination with a monoclonal antibody directed to the N-terminus or to the C-terminus of the molecule respectively.

In the assays described below NUNC Maxisorp, F 96 ELISA plate (cat. No. 439454) test plates were used and the antibody coating solution was prepared in sodium borate buffer (20 mM, pH 8.0, containing 0.1% sodium azide).

1. Plate Coating: Antibody selective for the particular human gastrin molecular form to be tested is coated at an optimal concentration onto the surface of the microwells of a test plate.

Optimal antibody concentration is determined by generating a standard curve using known concentrations of authentic gastrin hormone of the form to be assayed, the standard curve having the required sensitivity and precision over the required useful concentration range. For G17, the useful G17 concentration range of the assay is generally from background (about 4 pM or less) to about 25 pM, or about 50 pM. However, in patients with gastrin-producing tumors, the level of plasma gastrin hormone may be as high as 800 pM or even 1000 pM (1.0 micromolar). The determination of the appropriate sensitivity and precision over the required range can be readily determined by those of ordinary skill in the art without undue experimentation.

2. Plate washing: The coating solution is removed and wash buffer (approx. 400 µl per well) was added and then removed. This wash cycle is repeated as many times as required. Wash buffer was 0.010 M phosphate buffer; 0.0027M potassium chloride and 0.137M sodium chloride, pH 7.4, containing 0.01% w/v Triton X-100). Plate washing may be automated (the Labsystems Wellwash 4 Mk 2, Life Sciences International (UK) Ltd, Basingstoke, UK was used in the assays described below).

3. Plate blocking: Blocking buffer containing protein and detergent (1% BSA/0.1% Triton X-100 in coating buffer) is added to the microwells. Plates may be stored in this form.

4. Sample and standard addition: Plates are washed as described above. Assay buffer (1% BSA, 0.1% bovine γ-globulin and 200 KIU/ml aprotinin prepared in wash buffer) containing rabbit IgG (400 µg/ml), and EDTA (3.4 mM) is added to each well(100 µL/well). Test standards (such as, for instance, gastrin-depleted plasma to which has been added increasing amounts of authentic gastrin hormone) and test plasma samples are added to the wells (20 µL/well). The reaction is allowed to proceed overnight at nominally 4° C. Gastrin depletion of serum samples is readily achieved by allowing the samples to stand at room temperature overnight.

Dissociation peptide G17(1–9) (100 µg/ml) is included in the Assay buffer, rabbit IgG EDTA mix in those assays where total gastrin hormone (including antibody-bound gastrin hormone) is to be assayed.

5. Addition of conjugate: Following washing, assay buffer containing monoclonal or polyclonal antibody specific for the N-terminus of the gastrin hormone form to be assayed, conjugated with an enzyme label, and rabbit IgG (100 µg/ml) is added to each well. The reaction is allowed to proceed at room temperature (nominally +22° C.) with shaking using a microplate shaker. Examples of suitable enzyme substrates for use in development of the detection compound include nitro-phenylphosphate for alkaline phosphatase or tetramethylbenzidine sulfonate (TMBS) for horse-radish peroxidase. The degree of color development, sread as Absorbance Units (AU, read at 405 nm in the case of p-nitrophenol, or at 450 nm in the case of TNBS) is indicative of the amount of G17 present in the test sample, and the actual concentration is determined by reading absorbance of the test sample against a standard curve generated with known concentrations of gastrin hormone.

7. Reading: When sufficient assay signal has been obtained the signal is measured, e.g. by a microplate spectrophotometer or fluorimeter.

8. Data Processing: The assay signals obtained with known standard solutions of the gastrin hormone form are used to construct a calibration curve (signal vs. concentration). The calibration curve is used to interpolate concentrations of the gastrin hormone form in test samples.

The specific assay protocols for determining the amounts of total and free gastrin hormone forms are described below:

Determination of Total G17

Figure 1:
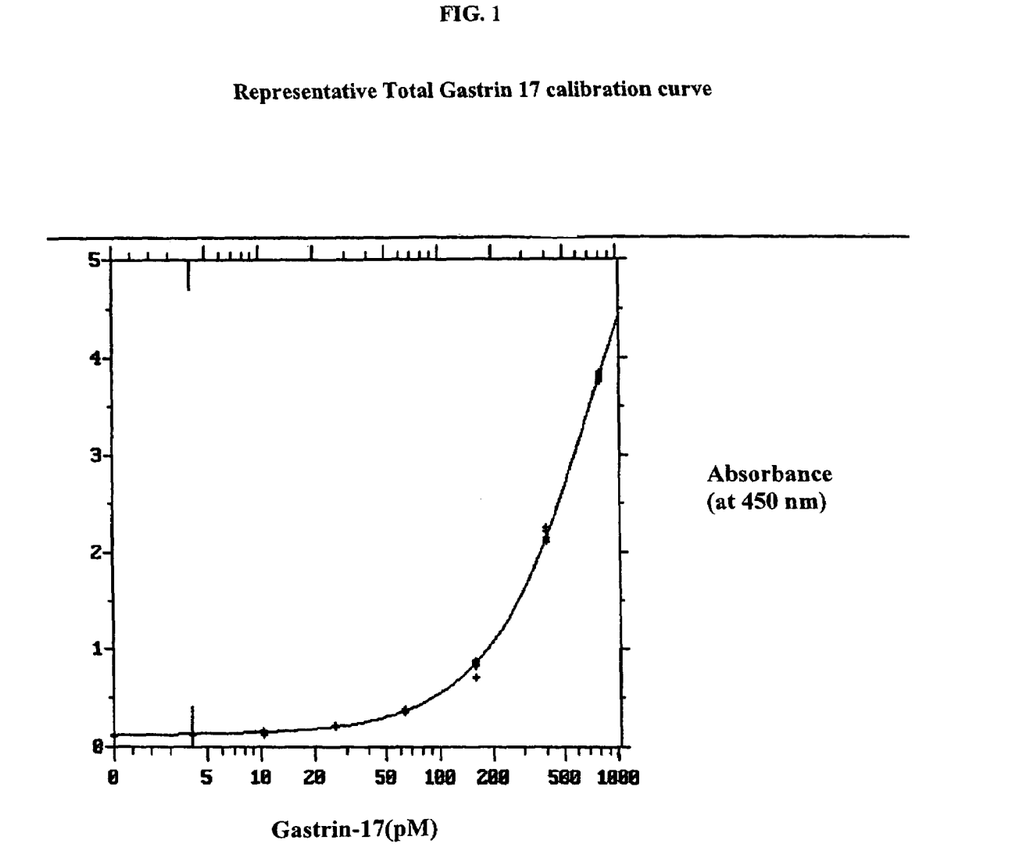
FIG. 1. A representative calibration curve for total gastrin-17 showing gastrin concentration in picomoles plotted against absorbance at 450 nm ($A_{450}$) following the enzyme catalyzed development using tetramethylbenzidine sulfonate (TMBS) as chromogenic substrate.

In this assay, antibody specific for the C-terminus of human gastrin-17 was coated onto the surface of the microwells of the test plate. Plate washing and plate blocking was performed as described for the general method above. Plates were washed as described. Assay buffer containing rabbit IgG (400 µg/ml), dissociation peptide $G17_{(1-9)}$ (100 µg/ml) and EDTA (3.4 mM) was added to each well (100 µL/well). Test standards (gastrin depleted plasma to which 0–4.1–10.2–26.6–64–160–400–1000 pM G17 had been added) and test plasma samples were added to the wells (20 µL/well). The reaction was allowed to proceed overnight in a refrigerator, at nominally 4° C. Following washing, assay buffer containing monoclonal antibody specific for the N-terminus of G17, conjugated with alkaline phosphatase, and rabbit IgG (100 µg/ml) was added to each well. Following washing, chromogenic substrate (pNPP) was added, the plates were incubated and allowed to develop color and read in a plate reader as described above. The assay signals obtained with known standard G17 solutions were used to construct a calibration curve (signal vs. concentration). This calibration curve was used to interpolate G17 concentrations in test samples. A representative calibration curve is shown in FIG. 1.

Determination of Free G17

Figure 2:
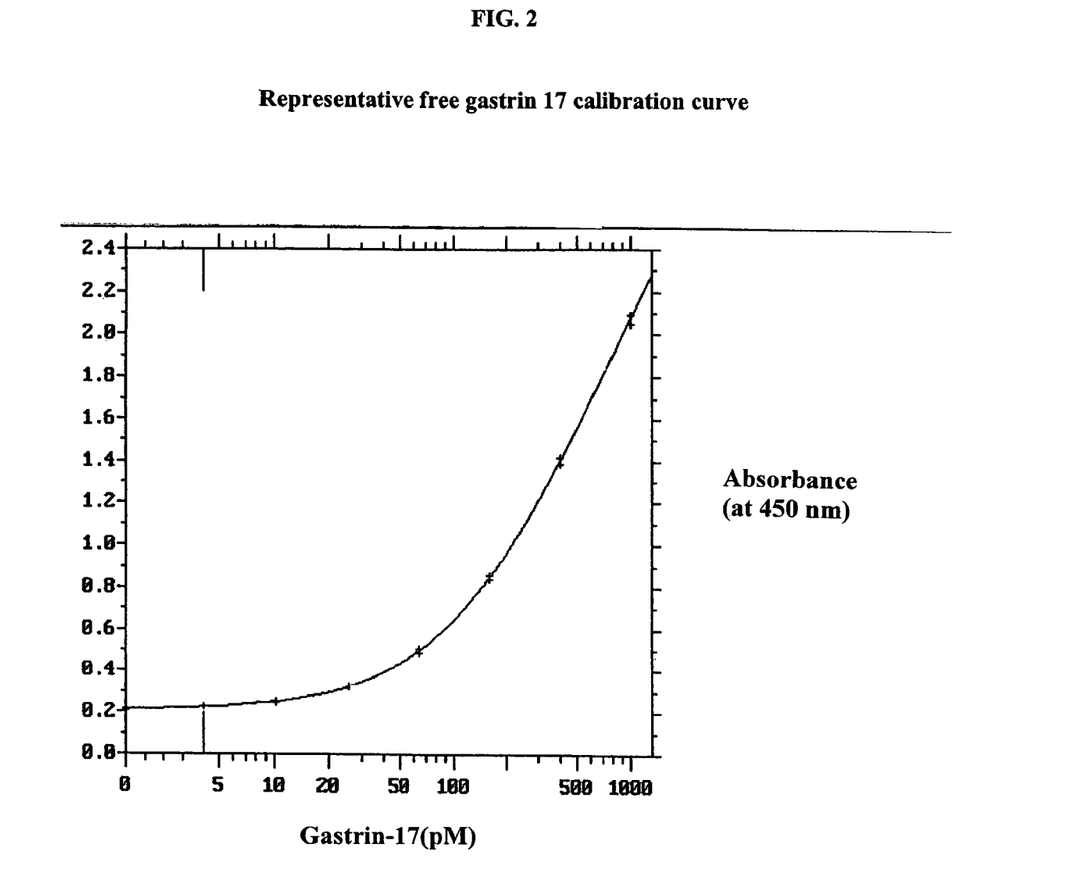
FIG. 2. A representative calibration curve for free gastrin-17 showing gastrin concentration in picomoles plotted against absorbance at 450 nm ($A_{450}$) as above.

Antibody specific for the N-terminus of the human gastrin-17 molecule was coated onto the surface of the microwells of a test plate. Plate washing and plate blocking was performed as described for the general method above. Plates were washed as described. Assay buffer (1% BSA, 0.1% bovine γ-globulin and 200 KIU/ml aprotinin prepared in wash buffer) containing rabbit IgG (400 µg/ml) was added and the reaction allowed to proceed at room temperature (nominally +22° C.), with shaking using a microplate shaker. Following washing, assay buffer containing monoclonal antibody specific for the C-terminus of G17, conjugated with alkaline phosphatase as enzyme label, and rabbit IgG (100 µg/ml) was added to each well. The reaction was allowed to proceed at room temperature (nominally +22° C.) with shaking using a microplate shaker. Following washing, chromogenic substrate (pNPP) was added, the plates were incubated and allowed to develop color and read in a plate reader as described above. The assay signals obtained with known standard G17 solutions were used to construct a calibration curve (signal vs. concentration) as in the assay for total G17 described above. The calibration curve was used to interpolate G17 concentrations in test samples. A representative calibration curve is shown in FIG. 2.

Determination of Total G17-Gly

Antibody specific for the C-terminus of the human glycine-extended gastrin-17 molecule was coated onto the surface of the microwells of a test plate as described above. Plate washing and plate blocking was performed as described for the general method above. Plates were washed as described. Assay buffer (1% BSA, 0.1% bovine γ-globulin and 200 KIU/ml aprotinin prepared in wash buffer) containing rabbit IgG (400 µg/ml), dissociation peptide $G17_{(1-9)}$ (100 µg/ml) and EDTA (3.4 mM) was added to each well (e.g. 100 µL/well). Test standards (gastrin depleted plasma to which had been added G17-gly at 0–4.1–10.2–26.6–64–160–400–1000 pM G17-Gly) and test plasma samples were added to the wells (e.g. 20 µL/well). The reaction was allowed to proceed overnight at nominally 4° C. Subsequent steps were exactly as described above for the assay for total G17.

Determination of Free G17-Gly

Antibody specific for the N-terminus of the G17-Gly molecule was coated onto the surface of the microwells of a test plate. Plate washing and plate blocking was performed as described for the general method above. Plates were washed as described. Assay buffer (1% BSA, 0.1% bovine γ-globulin and 200 KIU/ml aprotinin prepared in wash buffer) containing rabbit IgG (400 µg/ml) was added (e.g. 100 µl/well), followed by sample/standard (e.g. 50 µl/well) and the reaction allowed to proceed at room temperature (nominally +22° C.), with shaking using a microplate shaker. Following washing, assay buffer containing monoclonal antibody specific for the C-terminus of G17-Gly, conjugated with alkaline phosphatase, and rabbit IgG (100 µg/ml) was added to each well. The reaction was allowed to proceed at room temperature (nominally +22° C.) with shaking using a microplate shaker. Subsequent steps were exactly as described above for the assay for free G17.

Determination of G34

Antibody specific for the N-terminus of the human gastrin-34 was coated onto the surface of the microwells of a test plate. Plate washing and plate blocking was performed as described for the general method above. Plates were washed as described. Assay buffer (1% BSA, 0.1% bovine γ-globulin and 200 KIU/ml aprotinin prepared in wash buffer) containing rabbit IgG (400 µg/ml) was added (e.g. 100 µl/well), followed by sample/standard (e.g. 50 µl/well). The reaction was allowed to proceed at room temperature (nominally +22° C.), with shaking using a microplate shaker. Following washing, assay buffer containing monoclonal antibody specific for the C-terminus of G34, conjugated with alkaline phosphatase, and rabbit IgG (100 µg/ml) was added to each well and the reaction allowed to proceed at room temperature (nominally +22° C.) with shaking using a microplate shaker. Addition of the chromogenic substrate pNPP and reading of sample signal in the plate wells using a plate reader, and subsequent data processing was as described above. The assay signals obtained with known standard G34 solutions are used to construct a calibration curve (signal vs. concentration). The calibration curve is used to interpolate G34 concentrations in test samples.

EXAMPLES

Example 1

Determination of Total Gastrin 17 in Gastrin-Depleted Serum Samples to Which Known Amounts of Gastrin 17 had Been Added Serum was depleted of gastrin hormone by standing at room temperature overnight to allow endogenous proteases to completely degrade the gastrin hormone present.

To determine intra-assay precision and accuracy, known amounts of authentic gastrin 17 (G17) were added to replicate aliquots of the gastrin-depleted serum sample to achieve the nominal concentrations shown in Table 1. The assay for total G17 was performed using the N-terminal gastrin peptide in the same procedure as for serum samples containing anti-gastrin hormone antibody. The N-terminal gastrin peptide G17(1–9) was added at the steps of sample and standard addition as described above at a concentration of 100 µg/ml. The results, provided in Table 1, show that the assay accurately quantitated G17 within the accepted limits of ELISA methods, said ELISA limits being ±20% relative error. More importantly, the assay is most accurate at the concentrations of G17 at and below 100 pM, which (as noted above) are the concentrations normally found in patients.

TABLE 1

Total Gastrin 17 assay
Gastrin 17 concentration (pM)

|  | 7.50 | 15.00 | 100.0 | 600.0 | 720.0 |
|---|---|---|---|---|---|
| mean | 7.5 | 14.3 | 99.3 | 717.1 | 814.1 |
| sd | 0.8 | 0.9 | 1.7 | 16.2 | 7.7 |
| CV % | 11.2 | 6.5 | 1.7 | 2.3 | 0.9 |
| RE % | 0.0 | −4.7 | −0.7 | 19.5 | 13.1 | n = 6  Six replicate samples were assayed
sd     Standard deviation
CV     Coefficient of variation (calculated before rounding)
RE     Relative error (calculated after rounding)

Example 2

Determination of Free Gastrin 17 in Gastrin-Depleted Serum Samples to Which Known Amounts of Gastrin 17 had Been Added This assay was performed according to the method described in the "Assay Procedure" above for the determination of free gastrin-17 (G17). The results, provided in Table 2, show that the assay accurately quantitated free G17 within the accepted limits of ELISA methods. More importantly, the assay is most accurate at the concentrations of G17 at and below 100 pM, which are the concentrations normally found in patients.

TABLE 2

Free gastrin 17 assay
Inter-assay precision and accuracy data

Free gastrin 17 concentration (pM)

|  | 7.50 | 15.00 | 100.0 | 600.0 | 900.0 |
|---|---|---|---|---|---|
| mean | 7.55 | 13.41 | 94.01 | 556.6 | 892.8 |
| sd | 1.67 | 1.26 | 5.47 | 43.01 | 112.1 |
| CV % | 22.2 | 9.4 | 5.8 | 7.7 | 12.6 |
| RE % | 0.7 | −10.6 | −6.0 | −7.2 | −0.8 | n = 9  Nine replicate samples were assayed
sd     Standard deviation
CV     Coefficient of variation (calculated before rounding)
RE     Relative error (calculated after rounding)

Example 3

Gastrin-17 Stability

The stability of Gastrin at room temperature (about 22° C.) was assessed by the total gastrin assay as described above by measuring total G17 immediately after sample preparation (0 hour sample) to achieve known G17 concentrations of 15, 100 and 600 pM, and after 2 hours at room temperature on the bench. The results, demonstrating a substantial decrease in G17 concentration in each of the samples, are shown in Table 3, below. This demonstrates the importance of proper sample handling techniques, including minimal exposure to elevated temperatures when plasma is prepared from a sample of patients blood, to the accuracy of gastrin values obtained using the assay methods of the invention to test samples for gastrin hormone.

TABLE 3

Total Gastrin 17 assay
Stability of gastrin 17 in human plasma at room temperature (ca 22° C.)

Measured gastrin 17 concentration (pM)

|  |  | 15 | 100 | 600 |
|---|---|---|---|---|
| $0^a$ hours | mean | 11.6 | 89.4 | 605.5 |
|  | sd | 2.8 | 4.3 | 25.0 |
|  | CV(%) | 23.8 | 4.8 | 4.1 |
|  | RE(%) | −22.7 | −10.6 | 0.9 |
| 2 hours | mean | 5.5 | 59.1 | 400.5 |
|  | sd | 3.1 | 2.0 | 19.7 |
|  | CV(%) | 55.2 | 3.5 | 4.9 |
|  | RE(%) | −63.3 | −40.9 | −33.3 |

$^a$Mean result used as baseline
sd Standard deviation
CV Coefficient of variation (calculated before rounding)
RE Relative error (calculated after rounding)

Incorporation by Reference

All of the patents and publications cited in this specification are hereby expressly incorporated by reference in their entireties.

Deposit of Hybridoma Cell Lines

The following hybridomas that produce particular MAbs of the present invention were deposited with the American Type Culture Collection (ATCC, Manassas, Va.) on Mar. 25, 2004:

1. Hybridoma 400-1 produces MAb 400-1 that selectively binds an N-terminal epitope of G17 or Gly-extended G17 and is assigned accession number PTA-5889.

2. Hybridoma 400-2 produces MAb 400-2 that selectively binds an N-terminal epitope of G17 or Gly-extended G17 and is assigned accession number PTA-5890.

3. Hybridoma 400-3 produces MAb 400-3 that selectively binds an N-terminal epitope of G17 or Gly-extended G17 and is assigned accession number PTA-5891.

4. Hybridoma 400-4 produces MAb 400-4 that selectively binds an N-terminal epitope of G17 or Gly-extended G17 and is assigned accession number PTA-5892.

5. Hybridoma 401-2 produces MAb 401-2 that selectively binds an N-terminal epitope of G34 or Gly-extended G34 and is assigned accession number PTA-5893.

6. Hybridoma 445-1 produces MAb 445-1 that selectively binds a C-terminal epitope of Glycine-extended G17 or Gly-extended G34 and is assigned accession number PTA-5894.

7. Hybridoma 445-2 produces MAb 445-2 that selectively binds a C-terminal epitope of Glycine-extended G17 or Gly-extended G34 and is assigned accession number PTA-5895.

8. Hybridoma 458-1 produces MAb 458-1 that selectively binds a C-terminal epitope of G17 or G34 and is assigned accession number PTA-5896.

What is claimed is:

1. A method for determining the amount of free gastrin-17 (G17) or gastrin-34 (G34) in a biological fluid sample, comprising the steps of:

(a) obtaining a biological fluid sample comprising a gastrin hormone from a patient;

(b) providing an immobilized antibody selected from the group consisting of an immobilized antibody that selectively binds an N-terminal epitope of G17 and an immobilized antibody that selectively binds an N-terminal epitope of G34;

(c) incubating the sample to allow binding of G17 or G34 in the sample to said antibody to produce an immobilized complex of said antibody bound to the G17 or G34;

(d) washing the immobilized complex to remove unbound components, and reacting the complex with a detectable marker-conjugated monoclonal antibody that selectively binds a C-terminal epitope of G17 or G34, to form a detectable marker-conjugated antibody complex;

(e) washing the immobilized detectable marker-conjugated antibody complex, and incubating with a development reagent; and (f) measuring the developed reagent to determine the amount of free G17 or free G34 in the biological fluid sample;

wherein the monoclonal antibody that selectively binds a C-terminal epitope of G17 or G34 is the monoclonal antibody produced by the hybridoma 458-1 (ATCC accession no. PTA-5896).

2. The method of claim 1, wherein the immobilized antibody of step (b) is a monoclonal antibody.

3. The method of claim 2, wherein the immobilized monoclonal antibody selectively binds an N-terminal epitope of G17.

4. The method of claim 3, wherein the immobilized monoclonal antibody that selectively binds an N-terminal epitope of G17 is the antibody produced by the hybridoma 400-1 (ATCC accession no. PTA-5889), hybridoma 400-2 (ATCC accession no. PTA-5890), hybridoma 400-3 (ATCC accession no. PTA-5891) or the monoclonal antibody produced by the hybridoma 400-4 (ATCC accession no. PTA-5892).

5. The method of claim 2, wherein the monoclonal antibody selectively binds an N-terminal epitope of G34.

6. The method of claim 5, wherein the monoclonal antibody that selectively binds an N-terminal epitope of G34 is the monoclonal antibody produced by the hybridoma 401-2 (ATCC accession no. PTA-5893).

7. A method for determining the amount of free G34 in a biological fluid sample, comprising the steps of:

(a) obtaining a biological fluid sample comprising the gastrin hormone G34;

(b) providing an immobilized monoclonal antibody that selectively binds an N-terminal epitope of G34;

(c) incubating the sample to allow binding of the G34 in the sample to said antibody to produce an immobilized complex of said antibody bound to the G34;

(d) washing the immobilized complex to remove unbound components, and reacting the complex with a detectable marker-conjugated antibody that selectively binds a C-terminal epitope of G34, to form a detectable marker-conjugated antibody complex;

(e) washing the immobilized detectable marker-conjugated antibody complex, and incubating with a development reagent; and (f) measuring the developed reagent to determine the amount of free G34 in the biological fluid sample;

wherein the immobilized monoclonal antibody is the monoclonal antibody produced by the hybridoma 401-2 (ATCC accession no. PTA-5893).

8. The method of claim 7, wherein the antibody that selectively binds a C-terminal epitope of G34 is a monoclonal antibody.

9. The method of claim 8, wherein the monoclonal antibody that selectively binds a C-terminal epitope of G34 is the monoclonal antibody produced by the hybridoma 458-1 (ATCC accession no. PTA-5896).

10. A method for determining the amount of free Glycine-extended G17 or Glycine-extended G34 in a biological fluid sample, comprising the steps of:

(a) obtaining a biological fluid sample comprising a gastrin hormone from a patient;

(b) providing an immobilized antibody selected from the group consisting of an immobilized antibody that selectively binds an N-terminal epitope of Glycine-extended G17 and an immobilized antibody that selectively binds an N-terminal epitope of Glycine-extended G34;

(c) incubating the sample to allow binding of Glycine-extended G17 or Glycine-extended G34 in the sample to said antibody to produce an immobilized complex of said antibody bound to the Glycine-extended G17 or Glycine-extended G34;

(d) washing the immobilized complex to remove unbound components, and reacting the complex with a detectable marker-conjugated monoclonal antibody that selectively binds a C-terminal epitope of Glycine-extended G17 or Glycine-extended G34, to form a detectable marker-conjugated antibody complex;

(e) washing the immobilized detectable marker-conjugated antibody complex, and incubating with a development reagent; and (f) measuring the developed reagent to determine the amount of free Glycine-extended G17 or Glycine-extended G34 in the biological fluid sample;

wherein the monoclonal antibody is the monoclonal antibody produced by the hybridoma 445-1 (ATCC accession no. PTA-5894) or the monoclonal antibody produced by the hybridoma 445-2 (ATCC accession no. PTA-5895).

11. The method of claim 10, wherein the immobilized antibody of step (b) is a monoclonal antibody.

12. The method of claim 11, wherein the immobilized monoclonal antibody is a monoclonal antibody that selectively binds an N-terminal epitope of Glycine-extended G17.

13. The method of claim 12, wherein the immobilized monoclonal antibody that selectively binds an N-terminal epitope of Glycine-extended G 17 is the antibody produced by the hybridoma 400-1 (ATCC accession no. PTA-5889), hybridoma 400-2 (ATCC accession no. PTA-5890), hybridoma 400-3 (ATCC accession no. PTA-5891) or the monoclonal antibody produced by the hybridoma 400-4 (ATCC accession no. PTA-5892).

14. The method of claim 11, wherein the immobilized monoclonal antibody is a monoclonal antibody that selectively binds an N-terminal epitope of Glycine-extended G34.

15. The method of claim 14, wherein the immobilized monoclonal antibody that selectively binds an N-terminal epitope of Glycine-extended G34 is the monoclonal antibody produced by the hybridoma 401-2 (ATCC accession no. PTA-5893).

16. A method for determining the amount of free Glycine-extended G34 in a biological fluid sample, comprising the steps of:

(a) obtaining a biological fluid sample comprising the gastrin hormone Glycine-extended G34;

(b) providing an immobilized monoclonal antibody that selectively binds an N-terminal epitope of Glycine-extended G34;

(c) incubating the sample to allow binding of the Glycine-extended G34 in the sample to said antibody to produce an immobilized complex of said antibody bound to the Glycine-extended G34;

(d) washing the immobilized complex to remove unbound components, and reacting the complex with a detectable marker-conjugated antibody that selectively binds a C-terminal epitope of Glycine-extended G34, to form a detectable marker-conjugated antibody complex;

(e) washing the immobilized detectable marker-conjugated antibody complex, and incubating with a development reagent; and (f) measuring the developed reagent to determine the amount of free Glycine-extended G34 in the biological fluid sample;

wherein the immobilized monoclonal antibody is the monoclonal antibody produced by the hybridoma 401-2 (ATCC accession no. PTA-5893).

17. The method of claim 16, wherein the antibody that selectively binds a C-terminal epitope of Glycine-extended G34 is a monoclonal antibody.

18. The method of claim 17, wherein the monoclonal antibody that selectively binds a C-terminal epitope of Glycine-extended G34 is the monoclonal antibody produced by the hybridoma 445-1 (ATCC accession no. PTA-5894) or the monoclonal antibody produced by the hybridoma 445-2 (ATCC accession no. PTA-5895).

* * * * *

SEQUENCE LISTING

<160> NUMBER OF SEQ ID NOS: 8

<210> SEQ ID NO 1
<211> LENGTH: 17
<212> TYPE: PRT
<213> ORGANISM: Homo sapiens
<220> FEATURE:
<221> NAME/KEY: MOD_RES
<222> LOCATION: (1)..(1)
<223> OTHER INFORMATION: PYRROLIDONE CARBOXYLIC ACID
<220> FEATURE:
<221> NAME/KEY: MOD_RES
<222> LOCATION: (17)..(17)
<223> OTHER INFORMATION: AMIDATION

<400> SEQUENCE: 1

Glu Gly Pro Trp Leu Glu Glu Glu Glu Ala Tyr Gly Trp Met Asp
1               5                   10                  15

Phe

<210> SEQ ID NO 2
<211> LENGTH: 18
<212> TYPE: PRT
<213> ORGANISM: Homo sapiens
<220> FEATURE:
<221> NAME/KEY: MOD_RES
<222> LOCATION: (1)..(1)
<223> OTHER INFORMATION: PYRROLIDONE CARBOXYLIC ACID

<400> SEQUENCE: 2

Glu Gly Pro Trp Leu Glu Glu Glu Glu Ala Tyr Gly Trp Met Asp
1               5                   10                  15

Phe Gly

<210> SEQ ID NO 3
<211> LENGTH: 34
<212> TYPE: PRT
<213> ORGANISM: Homo sapiens
<220> FEATURE:
<221> NAME/KEY: MOD_RES
<222> LOCATION: (1)..(1)
<223> OTHER INFORMATION: PYRROLIDONE CARBOXYLIC ACID
<220> FEATURE:
<221> NAME/KEY: MOD_RES
<222> LOCATION: (34)..(34)
<223> OTHER INFORMATION: AMIDATION

<400> SEQUENCE: 3

Glu Leu Gly Pro Gln Gly Pro Pro His Leu Val Ala Asp Pro Ser Lys
1               5                   10                  15

Lys Glu Gly Pro Trp Leu Glu Glu Glu Glu Ala Tyr Gly Trp Met
            20                  25                  30

Asp Phe

<210> SEQ ID NO 4
<211> LENGTH: 35
<212> TYPE: PRT
<213> ORGANISM: Homo sapiens
<220> FEATURE:
<221> NAME/KEY: MOD_RES
<222> LOCATION: (1)..(1)
<223> OTHER INFORMATION: PYRROLIDONE CARBOXYLIC ACID

<400> SEQUENCE: 4

-continued

```
Glu Leu Gly Pro Gln Gly Pro Pro His Leu Val Ala Asp Pro Ser Lys
1               5                   10                  15

Lys Glu Gly Pro Trp Leu Glu Glu Glu Glu Ala Tyr Gly Trp Met
                20                  25                  30

Asp Phe Gly
        35

<210> SEQ ID NO 5
<211> LENGTH: 6
<212> TYPE: PRT
<213> ORGANISM: Homo sapiens
<220> FEATURE:
<221> NAME/KEY: MOD_RES
<222> LOCATION: (1)..(1)
<223> OTHER INFORMATION: PYRROLIDONE CARBOXYLIC ACID

<400> SEQUENCE: 5

Glu Gly Pro Trp Leu Glu
1               5

<210> SEQ ID NO 6
<211> LENGTH: 9
<212> TYPE: PRT
<213> ORGANISM: Homo sapiens
<220> FEATURE:
<221> NAME/KEY: MOD_RES
<222> LOCATION: (9)..(9)
<223> OTHER INFORMATION: AMIDATION

<400> SEQUENCE: 6

Glu Glu Ala Tyr Gly Trp Met Asp Phe
1               5

<210> SEQ ID NO 7
<211> LENGTH: 6
<212> TYPE: PRT
<213> ORGANISM: Homo sapiens
<220> FEATURE:
<221> NAME/KEY: MOD_RES
<222> LOCATION: (1)..(1)
<223> OTHER INFORMATION: PYRROLIDONE CARBOXYLIC ACID

<400> SEQUENCE: 7

Glu Leu Gly Pro Gln Gly
1               5

<210> SEQ ID NO 8
<211> LENGTH: 7
<212> TYPE: PRT
<213> ORGANISM: Homo sapiens

<400> SEQUENCE: 8

Tyr Gly Trp Met Asp Phe Gly
1               5
```